(12) United States Patent
Li et al.

(10) Patent No.: US 8,609,137 B2
(45) Date of Patent: Dec. 17, 2013

(54) SOFT CAPSULE OF BUTYLPHTHALIDE AND A PROCESS FOR PREPARING THE SAME

(75) Inventors: Jianqing Li, Shijiazhuang (CN); Min Bai, Shijiazhuang (CN); Wenmin Guo, Shijiazhuang (CN); Surui Chen, Shijiazhuang (CN); Liyun Liu, Shijiazhuang (CN); Guirong Zhou, Shijiazhuang (CN)

(73) Assignees: CSPC Zhongqi Pharmaceutical Technology (Shijiazhuang) Co., Ltd., Hebei (CN); CSPC NBP Pharmaceutical Co., Ltd., Hebei (CN)

( * ) Notice: Subject to any disclaimer, the term of this patent is extended or adjusted under 35 U.S.C. 154(b) by 8 days.

(21) Appl. No.: 13/092,610

(22) Filed: Apr. 22, 2011

(65) Prior Publication Data

US 2012/0052117 A1    Mar. 1, 2012

Related U.S. Application Data

(63) Continuation of application No. 11/445,832, filed on Jun. 2, 2006, now abandoned, which is a continuation of application No. PCT/CN2004/001411, filed on Dec. 3, 2004.

(30) Foreign Application Priority Data

Dec. 5, 2003    (CN) .......................... 2003 1 0119336

(51) Int. Cl.
*A61K 9/48*    (2006.01)
(52) U.S. Cl.
USPC ............................ 424/456; 424/451; 514/470

(58) Field of Classification Search
None
See application file for complete search history.

(56) References Cited

U.S. PATENT DOCUMENTS 4,366,145 A * 12/1982 Stoopak et al. ............... 424/455
6,096,338 A *  8/2000 Lacy et al. .................... 424/455

FOREIGN PATENT DOCUMENTS

CN             1375288 A  * 10/2002

OTHER PUBLICATIONS

Translation of CN1375288, orginal document published Oct. 2002.*
CAS Registry file for n-butylphthalide, accessed Aug. 1, 2008.*

* cited by examiner

*Primary Examiner* — Nissa Westerberg
(74) *Attorney, Agent, or Firm* — Edwards Wildman Palmer LLP; Ralph A. Loren, Esq.; Richard B. Emmons

(57) ABSTRACT

The present invention discloses a novel soft capsule of butylphthalide and a process for preparing the same. The soft capsule of butylphthalide is composed of a capsule wall material and a drug-containing oil, wherein the drug-containing oil is essentially composed of butylphthalide and a vegetable oil as the diluent in a weight ratio of about 1:0~10. The capsule wall material is composed of a capsule wall matrix, a plasticizer and water in a weight ratio of 1:0.2~0.4:0.8~1.3. The soft capsule of butylphthalide described in the present invention can mask the strong and special flavor of butylphthalide, and overcome the difficulties associated with formulating oily active ingredient into other oral formulation. The disintegration time of the soft capsule satisfies the requirement of Pharmacopoeia of P.R. China.

7 Claims, No Drawings

SOFT CAPSULE OF BUTYLPHTHALIDE AND A PROCESS FOR PREPARING THE SAME

PRIORITY INFORMATION

This application is a continuation of U.S. application Ser. No. 11/455,832, which was filed 2 Jun. 2006, now abandoned, which is a continuation of International Application No. PCT/CN2004/001411, which was filed on 3 Dec. 2004, which designated the United States and was published in Chinese, and which claims the benefit of Chinese Application CN200310119336.1, filed 5 Dec. 2003. The entire contents of the aforementioned patent applications are incorporated herein by this reference.

FIELD OF THE INVENTION

The present invention relates to a soft capsule of butylphthalide and a process for preparing the same.

BACKGROUND OF THE INVENTION

Butylphthalide is the main component of the celery and the seeds thereof. It may be obtained not only by direct extraction from the natural plant celery seed oil, but also by synthesis. Chinese Patent No. 98125618.X discloses the use of levo-butylphthalide in the manufacture of a medicament against thrombosis and platelet aggregation, and clearly shows that levo-butylphthalide has the effect on regulating the function of NOS-NO-cGMP system and the metabolism of arachidonic acid in neural cells after cerebral ischemia. Chinese Patent No. 93117148.2 discloses the use of butylphthalide in the manufacture of a medicament for preventing and treating diseases caused by cerebral ischemia in a mammal or human, wherein the butylphthalide has no optically active. Butylphthalide, an oily liquid with strong flavour of celery, is represented by the following chemical formula:

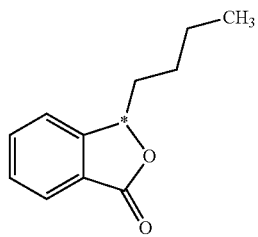 [SMILES: CCCC*1oc(=O)c2ccccc12]

The soft capsule, as a relatively novel dosage form, is particularly advantageous in the preparation of oily active ingredients into oral formulations, in which the active pharmaceutical ingredient is uniformly distributed in the diluent and fractional dose is accurate. Furthermore, the soft capsule has round and smooth shape, and is easy to be swallowed, which increases the compliance of patients.

SUMMARY OF THE INVENTION

The present inventors have developed a novel butylphthalide formulation, which is a soft capsule of butylphthalide, by taking advantages of physical and chemical properties of butylphthalide and the characteristics of soft capsules.

An object of the present invention is to provide a soft capsule of butylphthalide.

The soft capsule of butylphthalide according to the present invention is composed of a capsule wall material and a drug-containing oil, wherein the drug-containing oil is essentially composed of butylphthalide and a vegetable oil in an ratio of about 1:0-10 by weight. Furthermore, an appropriate antioxidant, butylated hydroxy toluene, may also be added into the drug-containing oil.

Term "butylphthalide" as used herein means racemic butylphthalide, levo-butylphthalide, or dextro-butylphthalide, which are all oily liquid.

The vegetable oil may be one of sesame oil, corn oil, peanut oil, soybean oil, almond oil, peach kernel oil, cottonseed oil, sunflower seed oil, olive oil, or the mixture thereof.

The capsule wall material is essentially composed of a capsule wall matrix, a plasticizer and water in a weight ratio of about 1:0.2~0.4:0.8~1.3. An appropriate preservative, such as ethyl p-hydroxybenzoate or methyl p-hydroxybenzoate, may also be added into the capsule wall material.

The capsule wall matrix may be one of gelatin and arabic gum, or the mixture thereof.

The plasticizer may be one of glycerol and sorbitol, or the mixture thereof.

The soft capsule of butylphthalide according to the present invention may be prepared by using the standard process for preparing soft capsules, such as hand compression molding, rotary compression molding or dropping molding. Generally, a compression process such as rotary compression molding using an automated rotary capsule machine controlled at 40-50° C. may be used, so that each capsule contains a pharmaceutically effective amount of butylphthalide.

The soft capsule is prepared as a novel formulation of butylphthalide according to the present invention. Such a soft capsule can mask the strong and special flavour of butylphthalide, and overcome the difficulties associated with formulating oily active agent into other oral formulation. Furthermore, the soft capsule has round and smooth shape, and is easy to be swallowed, which increases the compliance of patients.

DETAILED DESCRIPTION OF THE INVENTION

The soft capsule of butylphthalide according to the present invention is composed of a capsule wall material and a drug-containing oil, wherein the drug-containing oil is essentially composed of butylphthalide and a vegetable oil in an preferable weight ratio of about 1:1-8, more preferably about 1:2-5, most preferably about 1:3.5. Furthermore, as an antioxidant, about 0-0.2% of dibutylcarboxyl toluene relative to the weight of drug-containing oil may also be added into the drug-containing oil.

Preferably, the vegetable oil is peanut oil, soybean oil, corn oil, and sesame oil. Most preferably, the vegetable oil is soybean oil.

The capsule wall material is essentially composed of a capsule wall matrix, a plasticizer and water, wherein the capsule wall matrix is preferably gelatin, and the plasticizer is preferably glycerol.

The following examples are provided for a particular purpose of further illustrating technical features of the present invention, and should not be construed as any limitation to the present invention.

EXAMPLE 1

Preparation of Soft Capsules of Butylphthalide

Components of gelatin solution: 100 g of gelatin, 30 g of glycerol, 130 g of water 20 and 200 mg of ethyl p-hydroxybenzoate. Gelatin was added into an appropriate amount of water to permit it to absorb water and swell. Glycerol, ethyl p-hydroxybenzoate and remaining water were added into a melting tank and heated to 70-80° C. After uniformly mixed, the swollen gelatin was added, agitated, melted and incubated for 1-2 hours. The resulting mixture was thus kept standing to allow foams floating up. Then foams were removed by filtering through clean white cloth, and the temperature was kept for use. The gelatin solution was generally formulated at 2.8-3.2 rpm.

Preparation of drug-containing oil: 100 g of butylphthalide was weighed and 30 thoroughly mixed with 350 g of clear soybean oil, to obtain the drug-containing oil.

Compression of soft capsules: The gelatin solution and drug-containing oil were supplied into an automated rotary capsule machine. The temperature was kept at 40-50° C., and soft capsules were compressed, each of which contains 450 mg of drug-containing oil.

The soft capsules, compressed with the drug-containing oil by such a ratio, were tested and showed to have moderate shape and size and good content homogeneity. Results of the test were as following:

TABLE 1

| Sample | Caps. 1 | Caps. 2 | Caps. 3 | Caps. 4 | Caps. 5 | Caps. 6 | Caps. 7 | Caps. 8 | Caps. 9 | Caps. 10 |
| --- | --- | --- | --- | --- | --- | --- | --- | --- | --- | --- |
| Content (%) | 99.12 | 98.08 | 100.02 | 99.47 | 99.32 | 101.38 | 98.65 | 98.76 | 9925 | 98.47 |
| Range of content (%) | | | | | 98.08-101.38 | | | | | |
| Standard deviation (%) | | | | | 0.93 | | | | | |

EXAMPLE 2

Preparation of the Soft Capsules of Butylphthalide

The preparation procedure was the same as that described in Example 1, except that no vegetable oil was added in the step of preparing drug-containing oil. Each of the soft capsules finally compressed contains 100 mg of drug-containing oil.

EXAMPLE 3

Preparation of Soft Capsules of Butylphthalide

Preparation of gelatin solution: 100 g of gelatin, 40 g of glycerol, 120 g of water and 200 mg ethyl p-hydroxybenzoate were used. The steps for preparing gelatin 20 solution were the same as that described in Example 1.

Preparation of drug-containing oil: 225 g of butylphthalide was weighed and thoroughly mixed with 225 g of clear peanut oil, to obtain the drug-containing oil.

Compression of soft capsules: The procedure was the same as that described in Example 1, except that each of the soft capsules finally compressed contains 200 mg of drug-containing oil.

The soft capsules, compressed with the drug-containing oil by such a ratio, were tested, and results were as following:

TABLE 2

| Sample | Caps. 1 | Caps. 2 | Caps. 3 | Caps. 4 | Caps. 5 | Caps. 6 | Caps. 7 | Caps. 8 | Caps. 9 | Caps. 10 |
| --- | --- | --- | --- | --- | --- | --- | --- | --- | --- | --- |
| Content (%) | 98.33 | 96.08 | 99.42 | 101.73 | 94.37 | 100.31 | 92.65 | 98.79 | 102.01 | 95.78 |
| Range of content (%) | | | | | 92.65-102.01 | | | | | |
| Standard deviation (%) | | | | | 3.14 | | | | | |

EXAMPLE 4

Preparation of Soft Capsules of Butylphthalide

The preparation procedure was the same as that described in Example 1, except that in the step of preparing the drug-containing oil, 56.25 g of butylphthalide was weighed and thoroughly mixed with 393.75 g of clear peanut oil. Each of the soft capsules finally compressed contains 800 mg of drug-containing oil.

The soft capsules, compressed with the drug-containing oil in such a ratio, were tested, and results were as following:

TABLE 3

| Sample | Caps. 1 | Caps. 2 | Caps. 3 | Caps. 4 | Caps. 5 | Caps. 6 | Caps. 7 | Caps. 8 | Caps. 9 | Caps. 10 |
|---|---|---|---|---|---|---|---|---|---|---|
| Content (%) | 100.03 | 99.08 | 99.42 | 101.73 | 98.57 | 100.31 | 99.55 | 98.99 | 100.11 | 99.98 |
| Range of content (%) | | | | | 98.57-101.73 | | | | | |
| Standard deviation (%) | | | | | 0.88 | | | | | |

EXAMPLE 5

Preparation of Soft Capsules of Butylphthalide

Preparation of gelatin solution: 100 g of gelatin, 20 g of glycerol, 80 g of water and 200 mg of ethyl p-hydroxybenzoate were used. The steps for preparing gelatin solution were the same as that described in Example 1.

Preparation of drug-containing oil: 45 g of butylphthalide was weighed and thoroughly mixed with 405 g of clear peanut oil, to obtain the drug-containing oil.

Compression of soft capsules: The procedure was the same as that described in Example 1, except that each of soft capsules finally compressed contains 1000 mg drug-containing oil.

EXAMPLE 6

Preparation of Soft Capsules of Butylphthalide

The preparation procedure was the same as that described in Example 1, except that in the step of preparing the drug-containing oil, 90 g of butylphthalide was weighed and thoroughly mixed with 360 g of clear soybean oil. Each of soft capsules finally compressed contains 500 mg of drug-containing oil.

EXAMPLE 7

Preparation of Soft Capsules of Butylphthalide

The preparation procedure was the same as that described in Example 1, except that in the step of preparing the drug-containing oil, 40.91 g of butylphthalide was weighed and thoroughly mixed with 409.09 g of clear soybean oil. Each of soft capsules finally compressed contains 1100 mg of drug-containing oil.

EXAMPLE 8

Preparation of Soft Capsules of Butylphthalide

The preparation procedure was the same as that described in Example 1, except that in the step of preparing the drug-containing oil, 50 g of butylphthalide was weighed and thoroughly mixed with 400 g of clear soybean oil. Each of soft capsules finally compressed contains 900 mg of drug-containing oil.

EXAMPLE 9

Preparation of Soft Capsules of Butylphthalide

The preparation procedure was the same as that described in Example 1, except that in the step of preparing the drug-containing oil, 150 g of butylphthalide was weighed and thoroughly mixed with 300 g of clear soybean oil and 0.45 g of dibutylcarboxyl toluene as an antioxidant. Each of soft capsules finally compressed contains 300.3 mg of drug-containing oil.

EXAMPLE 10

Test of Butylphthalide Content, Related Materials and Disintegration Time

Determination Method

A) Disintegration Time: Samples prepared in Example 1 were provided. Time required for complete disintegration of each soft capsule was tested in accordance with the disintegration time assay (Pharmacopoeia of P.R. China, the edition of 2000, Part II, Appendix VA), with 1000 ml of diluted hydrochloric acid (9 to 1000) as solvent, the temperature was controlled at 37±1° C., the lift-and-drop rate of 30 to 32 times per minute, and with a baffle plate when operated. Time required by complete disintegration of each soft capsule was investigated. The disintegration time should not be over 1 hour, and should comply with the corresponding regulations.

B) Related Materials: Tests were performed according to High Performance Liquid Chromatography (Pharmacopoeia of P.R. China, the edition of 2000, Part II, 30 Appendix VD).

Testing Method: Appropriate amount of the content of capsules was sampled, appropriate amount of chloroform was added into it to dissolve, and then methanol was added to supplement the volume. The resulting solution was diluted with methanol to formulate a testing solution containing 0.5 mg of the content per milliliter. Appropriate amount of butylphthalide control was separately and precisely weighed, dissolved with methanol and formulated into a control solution containing 15 μg of butylphthalide per milliliter. 20 μl of control solution was accurately injected into the liquid chromatograph and tested according to the method known in the art. The detection sensitivity was adjusted in order to make the peak of the main fraction as high as 10-20% of full range. 20 μl of testing solution was accurately taken and tested according to the same method. Chromatographic spectrum was recorded for two times of the retention time of the main fraction peak in chromatography. If impurities presented in chromatographic spectrum, the area sum under the peak of each impurity (with the exception of the peak of solvent) was calculated; should be not more than the area of that of control solution (3.0%).

C) Determination of butylphthalide content: The content was determined by High Performance Liquid Chromatography (Pharmacopoeia of P.R. China, the edition of 20 2000, Part II, Appendix VD).

Chromatographic Condition And System Suitability Test: Silica gel bonded with octodecyl silane was used as packing, methanol-water (65:35) was used as mobile phase with a flow rate of 1.0 ml/min. The detection was performed at the 25 wavelength of 280 nm. Theoretical plate number of butylphthalide should be not less than 1500. The degree of separating butylphthalide from impurities should comply with related regulations.

Preparation of Control Solution: 50 mg of butylphthalide was precisely weighed and 30 placed into a 50 ml measuring flask. The weighed butylphthalide is dissolved with methanol and diluted to the predetermined value of scale, and mixed uniformly. 5 ml of resulting solution was precisely taken and placed into a 50 ml measuring flask, diluted with methanol to the predetermined value of scale, and thus the control solution was obtained.

Preparation of Test Solution: Appropriate amount of the content in capsules (approximately 50 mg of butylphthalide) was taken and precisely weighed. The weighed content is placed into a 50 ml measuring flask, dissolved with appropriate amount of chloroform, diluted with methanol to the predetermined value of scale and thoroughly mixed. 5 ml of resulting solution was precisely taken and placed into a 50 ml measuring flask, diluted with methanol to the predetermined value of scale, and thus the test solution was obtained.

Testing Method: 20 μl of control solution and 20 μl of test solution separately were precisely sampled and injected into the liquid chromatograph, and then tested according to the method known in the art. The chromatographic spectrum was recorded, and the content of butylphthalide ($C_{12}H_{14}O_2$) was calculated with peak area in accordance with external standard method.

The experimental data were represented as following:

TABLE 4

| Test condition | | | Content (%) | Content of Related material (%) | Disintegration time |
|---|---|---|---|---|---|
| Environment | Time | Appearance | | | |
| Initial | Day 0 | Yellow, transparent soft capsule | 98.8 | 0.61 | 4'50" |
| Accelerating test | 1 mon. | Yellow, transparent soft capsule | 98.7 | 0.66 | 6'45" |
| | 2 mon. | Yellow, transparent soft capsule | 99.3 | 0.63 | 14'10" |
| | 3 mon. | Yellow, transparent soft capsule | 98.4 | 0.62 | 28'30" |
| | 6 mon. | Yellow, transparent soft capsule | 99.0 | 0.58 | 49'52" |
| Sample at room temperature | 1 mon. | Yellow, transparent soft capsule | 98.6 | 0.63 | 5'15" |
| | 3 mon. | Yellow, transparent soft capsule | 98.8 | 0.67 | 8'35" |
| | 6 mon. | Yellow, transparent soft capsule | 99.4 | 0.66 | 9'45" |
| | 12 mon. | Yellow, transparent soft capsule | 99.1 | 0.62 | 17'50" |
| | 18 mon. | Yellow, transparent soft capsule | 98.5 | 0.64 | 27'25" |
| | 24 mon. | Yellow, transparent soft capsule | 98.5 | 0.65 | 29'35" |

Although frequently soft capsules have the problem of unqualified disintegration due to the prolonged time of storage, as shown in the accelerating test and long period test on the present soft capsules, the wall of the soft capsule aged quickly with heating treatment and disintegration time changed significantly but still remained less than 60 minutes, which complied with related regulations of Pharmacopoeia of P.R. China, the edition of 2000. Various parameters, such as product appearance, the content and related materials and the like all complied with the standard, with a valid period up to 2 years.

The invention claimed is:

1. A soft capsule comprising a capsule wall and a drug-containing oil, wherein the drug-containing oil consists of butylphthalide and a vegetable oil in a weight ratio of 1:1 to 1:10, and wherein the capsule wall comprises gelatin, glycerol and water in a weight ratio of 1:0.2-0.4:0.8-1.3.

2. The soft capsule of claim 1, wherein the weight ratio of butylphthalide to vegetable oil is 1:1 to 1:8.

3. The soft capsule of claim 2, wherein the weight ratio of butylphthalide to the vegetable oil is 1:2 to 1:5.

4. The soft capsule of claim 3, wherein the weight ratio of butylphthalide to the vegetable oil is 1:3.5.

5. The soft capsule of claim 1, wherein the vegetable oil is selected from the group consisting of sesame oil, corn oil, peanut oil, soybean oil, almond oil, peach kernel oil, cotton seed oil, sunflower seed oil, olive oil and mixtures thereof.

6. The soft capsule of claim 1, wherein the butylphthalide is selected from the group consisting of racemic butylphthalide, levo-butylphthalide and dextro-butylphthalide.

7. The soft capsule of claim 1, wherein the capsule wall further comprises a preservative.

* * * * *